United States Patent [19]

Yuen

[11] Patent Number: 4,988,722
[45] Date of Patent: Jan. 29, 1991

[54] PARENTERAL COMPOSITIONS

[75] Inventor: Pui-Ho Yuen, Princeton Junction, N.J.

[73] Assignee: Schering Corporation, Kenilworth, N.J.

[21] Appl. No.: 416,553

[22] Filed: Oct. 3, 1989

[51] Int. Cl.$^5$ .............................................. A61K 31/41
[52] U.S. Cl. .................................................. 514/383
[58] Field of Search ........................................ 514/383

[56] References Cited

FOREIGN PATENT DOCUMENTS 0178533  4/1986  European Pat. Off. .

OTHER PUBLICATIONS

Chemical Abstracts: vol. 105: 35613r (1986).

Primary Examiner—Douglas W. Robinson
Assistant Examiner—Kevin Weddington
Attorney, Agent, or Firm—John J. Maitner; Stephen I. Miller; James R. Nelson

[57] ABSTRACT

A process for preparing aqueous parenteral compositions of drugs which are weak bases and are only slightly soluble in water is disclosed. Aqueous parenteral compositions of the antifungal agent (±) (2R*, 3R*)-2-(2,4-difluorophenyl)-3-methylsulfonyl-1-(1,2,4-triazol-1-yl)butan-2-ol are also disclosed.

5 Claims, No Drawings

PARENTERAL COMPOSITIONS

The present invention relates to aqueous parenteral compositions of drugs which are weak bases and are only slightly soluble in water. More particularly, the invention relates to aqueous parenteral compositions of the compound (±)-(2R*,3R*)-2-(2,4-difluorophenyl)-3-methylsulfonyl-1-(1,2,4-triazol-1-yl)butan-2-ol (hereinafter Compound 1).

Compound 1 is useful in the treatment of fungal infections. European patent application No. 178,533 published Apr. 23, 1986 discloses Compound 1, its preparation and the use of the compound as an antifungal agent.

Compound 1 is a weak base which is very slightly soluble in water, e.g. 0.15 mg/ml. The solubility profile of Compound 1 in strong acids indicates that the solubility increases with acid concentration and with decreasing pH. At pH 1 in 0.15 M hydrochloric acid, the solubility of Compound 1 increases to about 0.7 mg/ml. The use of such a highly acidic aqueous solution for parenteral administration is not practical.

The preparation of a more concentrated aqueous solution of Compound 1, e.g. 0.6–0.8 mg/ml at pH 5 to 8, has proven difficult due to the slight solubility of the compound in water. Attempts to prepare such solutions by use of surfactants and complexing agents have proven unsuccessful since the desired concentration of drug could not be obtained.

It is an object of the present invention to provide aqueous parenteral compositions of drugs which are weakly base and are only slightly soluble in water.

It is an object of the present invention to provide an aqueous small volume parenteral composition of Compound 1, e.g. about 100 ml, which is capable of delivering 50 mg of the drug. The compositions of the present invention should have pH of from 5 to 8, and must be physically stable for up to 8 hours after preparation, i.e. preparation of the composition.

SUMMARY OF THE INVENTION

The present invention provides a process for the preparation of aqueous parenteral compositions of drugs which are weak bases and are only slightly soluble in water. The process comprises mixing a basic aqueous alkali metal salt solution with an aqueous acidic solution of a drug which is a weak base and only slightly soluble in water, a mineral acid and a compound which is capable of provide buffering action at a pH of from 5 to 8 after the solutions are mixed.

The present invention also provides aqueous parenteral compositions of Compound 1 which are useful in treating fungal infections. The composition comprises a supersaturated aqueous solution.

| Ingredient | mg/ml |
| --- | --- |
| Compound 1 | 0.48 |
| Sodium Chloride | 7.00 |
| Sodium Phosphate Monobasic | 5.90 |
| Sodium Phosphate DiBasic | 1.50 |
| Water for Injection | q.s. 1.00 |

The resulting composition has a pH from 5–8 and is physically stable for up to 8 hours.

The present invention is also directed to a kit consisting of two vials; one vial comprising Compound 1, hydrochloric acid, phosphoric acid and water for injection; and a second vial comprising a sodium hydroxide solution. Mixing the contents of the two vials produces the parenteral compositions of the present invention.

DETAILED DESCRIPTION OF THE INVENTION

The present invention provides a process for the preparation of aqueous parenteral compositions of drugs which are weak bases and are only slightly soluble in water. The process comprises mixing an aqueous alkali metal salt solution with an aqueous acidic solution of a drug which is a weak base and only slightly soluble in water, a mineral acid and a compound which is capable of provide buffering action at a pH of from 5 to 8 after the solutions are mixed.

The present invention provides a supersaturated aqueous parenteral composition of Compound 1 which is physically stable for up to 8 hours after mixing.

The parenteral composition of the invention comprise an aqueous solution having the following ingredients:

| Ingredient | mg/ml |
| --- | --- |
| Compound 1 | 0.48 |
| Sodium Chloride | 7.00 |
| Sodium Phosphate Monobasic | 5.90 |
| Sodium Phosphate DiBasic | 1.50 |
| Water for Injection | q.s. 1.00 | which has a pH of from 5–8, and is physically stable up to 8 hours after preparation.

In preparing the parenteral compositions of the present invention, two solutions are prepared. The first solution comprises the active drug component, Compound 1, in an aqueous solution of a strong mineral acid and a compound which is capable of providing buffering capacity at a pH of from 5 to 8 after the acidic solution is neutralized with base prior to administration.

Examples of strong mineral acids useful in the present invention include hydrochloric acid, sulfuric acid and phosphoric acid; the preferred mineral acid is hydrochloric acid.

The amount of acid added required to prepare the solution containing the drug will depend on the final concentration of drug in the parenteral composition. The calculation is well within the knowledge of one of ordinary skill in the art.

The compound capable of providing buffering capacity to maintain the pH of from 5 to 8 of the compositions of the present invention is phosphoric acid, which after neutralizing the acid solution with base results in the formation of monobasic and dibasic sodium phosphate. The buffering action of the phosphate combination maintains the pH of the parenteral compositions of the present invention at pH 6.0 and 6.8. The ionic composition of this solution is isotonic.

The basic solution utilized in the neutralization of the acidic solution containing Compound 1 comprises an aqueous solution of an alkali metal salt, such as sodium hydroxide or potassium hydroxide. The preferred base in carrying out the invention is sodium hydroxide.

The parenteral compositions of this invention are prepared by mixing the aqueous acidic solution containing Compound 1, the mineral acid and the compound which provides buffering capacity with the aqueous basic solution. Preferably the basic solution is added to the acidic solution to neutralize said acidic solution. Mixing of the two solutions is carried out at room temperature under sterile or aseptic conditions.

The resulting parenteral solution is a clear, colorless supersaturated aqueous solution of Compound 1 having a pH of from 5 to 8, preferably pH 6.0 to 6.8, and is physically stable up to 8 hours. In the context of this invention, the term "physically stable" means that the parenteral solution is free of solid particles of Compound 1.

The compositions of the present invention are primarily intended for use by parenteral administration, e.g. intravenous infusion. The formulations may be administered by infusion over a period of time from several minutes to several hours.

The following non-limiting example illustrates the preparation of parenteral compositions of the present invention.

EXAMPLE 1

A parenteral composition was prepared in the following manner:

| 1. SOLUTION A: | |
|---|---|
| Ingredients | Concentration (g/1.0 liter) |
| Compound 1, micronized | 0.6 |
| Hydrochloric Acid NF (37% solution) | 14.87 |
| Phosphoric Acid NF (85% solution) | 8.52 |
| Water For Injection | q.s. To make 1.0 liter |

Charge approximately 800 ml of water for injection to a vessel. The hydrochloric acid is dispersed in the water. Compound 1 is dissolved in the acidic solution with stirring. The phosphoric acid is dispersed in the solution and the solution is brought to final volume with water for injection. The solution is mixed and aseptically filtered. The filtrate is collected in a sterilized filling vessel and the solution aseptically filled into sterilized vials using a nominal fill volume of 90 ml. The vials are then aseptically sealed.

| 1. SOLUTION B: | |
|---|---|
| Components | Concentration (g/1.0 liter) |
| Sodium Hydroxide, NF Pellets | 40.0 |
| Water for Injection USP | q.s. To make 1.0 liter |

Charge approximately 900 ml of water for injection to a suitable vessel. Dissolve the sodium hydroxide pellets in the water. Bring the solution to final volume with water for injection and mix the solution. Aseptically filter the solution and collect the filtrate in a sterilized filling vessel. Aseptically fill the solution into vials with a nominal fill volume of 23 ml.

At the time of administration, one vial (23 ml) of Solution B (containing 40 mg/ml of sodium hydroxide) is transferred into one vial (90 ml) of Solution A (containing 0.6 mg/ml of Compound 1) using an appropriate sterilized transfer device.

The resulting parenteral solution comprises:

| Ingredient | mg/113 ml solution | mg/ml |
|---|---|---|
| Compound 1 | 54 | 0.48 |
| Sodium Chloride | 791 | 7.00 |
| Sodium Phosphate Monobasic | 667 | 5.90 |
| Sodium Phosphate DiBasic | 170 | 1.50 |
| Water for Injection | 113 ml | qs 1.00 ml |

The solution is administered by intravenous infusion using an I.V. administration set. The average total volume delivered to the patient is 105 ml which contains 50 mg of Compound 1.

I claim:

1. A process for the preparation of an aqueous parenteral composition of the drug (±) (2R*,3R*)-2-(2,4-difluorophenyl) -3-methylsulfonyl-1-(1,2,4-triazol-1-yl)-butan-2-ol which comprises mixing an aqueous solution of an alkali metal salt selected from the group consisting of sodium hydroxide and postassium hydroxide, with an aqueous acid solution of the drug, a mineral acid selected from the group consisting of hydrochloric acid and sulfuric acid, and a compound capable of providing buffering action at a pH of from 5 to 8 after the solutions are mixed, said composition being physically stable for up to 8 hours.

2. The process of claim 1 wherein the mineral acid is hydrochloric acid, the compound capable of providing buffering action is phosphoric acid and the alkali metal salt is sodium hydroxide.

3. An aqueous parenteral composition comprising:

| Ingredient | mg/ml |
|---|---|
| (±) (2R*, 3R*)-2-(2,4-difluorophenyl)-3-methylsulfonyl-1-(1,2,4-triazol-1-yl) butan-2-ol | 0.48 |
| Sodium Chloride | 7.00 |
| Sodium Phosphate Monobasic | 5.90 |
| Sodium Phosphate DiBasic | 1.50 |
| Water for Injection | qs 1.00 | having a pH of 5 to 8 and is physically stable for up to 8 hours.

4. The parenteral composition of claim 3 wherein the pH is 6.2 to 6.8.

5. The parenteral composition of claim 3 prepared by a process which comprises mixing:

| Components | Concentration (g/1.0 liter) |
|---|---|
| Solution A: | |
| (±) (2R*, 3R*)-2-(2,4-difluorophenyl)-3-methylsulfonyl-1-(1,2,4-triazol-1-yl) butan-2-ol | 0.6 |
| Hydrochloric Acid NF (37% solution) | 14.87 |
| Phosphoric Acid NF (85% solution) | 8.52 |
| Water for Injection | q.s. To make 1.0 liter |
| with Solution B | |
| Sodium hydroxide NF Pellets | 40.0 |
| Water for Injection | q.s To make 1.0 liter | to produce a clear, colorless solution having a pH of 6.0 to 6.8 and being physically stable for up to 8 hours.

* * * * *